(12) United States Patent
Poteet, III et al.

(10) Patent No.: US 11,763,390 B2
(45) Date of Patent: Sep. 19, 2023

(54) INTELLIGENTLY LINKING PAYER/HEALTH PLAN COMBINATIONS TO SPECIFIC EMPLOYERS

(71) Applicant: CERNER INNOVATION, INC., Kansas City, KS (US)

(72) Inventors: James L. Poteet, III, Overland Park, KS (US); Raymond G. Delano, III, Leawood, KS (US); Julie Ann Jensen, Olathe, KS (US)

(73) Assignee: CERNER INNOVATION, INC., Kansas City, MO (US)

( * ) Notice: Subject to any disclaimer, the term of this patent is extended or adjusted under 35 U.S.C. 154(b) by 181 days.

(21) Appl. No.: 16/812,535

(22) Filed: Mar. 9, 2020

(65) Prior Publication Data

US 2021/0202053 A1 Jul. 1, 2021

Related U.S. Application Data

(60) Provisional application No. 62/955,590, filed on Dec. 31, 2019.

(51) Int. Cl.
*G06Q 40/08* (2012.01)
*G16H 10/60* (2018.01)
*G06N 20/00* (2019.01)
*G06Q 20/40* (2012.01)
*G06F 18/213* (2023.01)

(52) U.S. Cl.
CPC ........... *G06Q 40/08* (2013.01); *G06F 18/213* (2023.01); *G06N 20/00* (2019.01); *G06Q 20/401* (2013.01); *G16H 10/60* (2018.01)

(58) Field of Classification Search
CPC .... G06N 20/00; G06K 9/6232; G06Q 20/401; G06Q 40/08
USPC .......................................................... 705/3
See application file for complete search history.

(56) References Cited

U.S. PATENT DOCUMENTS

| 7,392,237 | B2 | 6/2008 | Pratt |
| 7,580,831 | B2 | 8/2009 | Haskell et al. |
| 7,970,629 | B2 | 6/2011 | Christen |
| 8,751,250 | B2 | 6/2014 | Lutzen et al. |
| 9,721,315 | B2 | 8/2017 | Christen |
| 2016/0063636 | A1 | 3/2016 | Feimster et al. |

(Continued)

*Primary Examiner* — Edward Chang
(74) *Attorney, Agent, or Firm* — KRAGULJAC LAW GROUP, LLC (57) ABSTRACT

Methods, computer systems, and computer storage media are provided for utilizing machine learning to verify payers and/or health plans. HIPAA transactions can be utilized to train a machine learning model to intelligently link payers and/or health plans to specific employers. Initially, transaction data is received from electronic data interchange (EDI) insurance transactions. The transaction data comprises data corresponding to a plurality of employers, a plurality of payers, and a plurality of health plans provided by the plurality of payers. A machine learning model is trained with the transaction data to build a mapping of the plurality of employers, the plurality of payers contracted with each employer of the plurality of employers, and the plurality of health plans provided by the plurality of payers for each employer of the plurality of employers. The machine learning model is utilized to verify the scan data is mapped in accordance with the mapping.

18 Claims, 4 Drawing Sheets (56) References Cited

U.S. PATENT DOCUMENTS

2019/0080416 A1\* 3/2019 Smith .................... G16H 50/70
2019/0095822 A1  3/2019 Rugel et al.

\* cited by examiner

INTELLIGENTLY LINKING PAYER/HEALTH PLAN COMBINATIONS TO SPECIFIC EMPLOYERS

BACKGROUND

Health care providers are dependent on accurate insurance information to ensure their medical claim reimbursements are timely paid. Such timeliness enables health care providers to predict cash flow. Often patient insurance eligibility and health care claims are sent to the wrong payer or health plan, resulting in denied claims. This situation may happen if the health plan on the insurance card cannot be matched to a health plan in the electronic health record system (EHR). Or, perhaps the health plan was built in the EHR using a slightly different name or is abbreviated or confused with or similarly named plan. Similar situations may arise if the patient is from a different state or locality and the provider organization has not built a particular health plan in the EHR. Sometimes, the health insurance card is scanned correctly but still manually matched to the wrong health plan and/or the electronic routing is configured incorrectly. In each of these scenarios, the health care provider is not likely to receive timely reimbursement and a budget shortfall results.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to utilizing machine learning to verify payers and/or health plans. More particularly, the present invention utilizes HIPAA transactions to train a machine learning model to intelligently link payers and/or health plans to specific employers. Initially, transaction data is received from electronic data interchange (EDI) insurance transactions. The transaction data comprises data corresponding to a plurality of employers, a plurality of payers, and a plurality of health plans provided by the plurality of payers. A machine learning model is trained with the transaction data to build a mapping of the plurality of employers, the plurality of payers contracted with each employer of the plurality of employers, and the plurality of health plans provided by the plurality of payers for each employer of the plurality of employers. The machine learning model can be utilized to verify the scan data is mapped in accordance with the mapping.

BRIEF DESCRIPTION OF THE SEVERAL VIEWS OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

As noted in the Background, health care providers are dependent on accurate insurance information to ensure medical claim reimbursements are timely paid. Such timeliness enables health care providers to predict cash flow. Often patient insurance eligibility and health care claims are sent to the wrong payer or health plan, resulting in denied claims. For example, if the health plan on the insurance card cannot be matched to a health plan in the electronic health record system, the claim may be denied. In another example, if the health plan was built in the EHR using a slightly different name or is abbreviated or confused with or similarly named plan, the claim may be denied. The claim may also be denied if the patient is from a different state or locality and the provider organization has not built a particular health plan in the EHR. Even if the health insurance card is scanned correctly, it may be manually matched to the wrong health plan and/or the electronic routing is configured incorrectly, and the claim may be denied. In each of these scenarios, the health care provider is not likely to receive timely reimbursements and a budget shortfall results.

Embodiments of the present invention relate to utilizing machine learning to verify payers and/or health plans. More particularly, the present invention utilizes HIPAA transactions to train a machine learning model to intelligently link payers and/or health plans to specific employers. Initially, transaction data is received from EDI insurance transactions. The transaction data comprises data corresponding to a plurality of employers, a plurality of payers, and a plurality of health plans provided by the plurality of payers. A machine learning model is trained with the transaction data to build a mapping of the plurality of employers, the plurality of payers contracted with each employer of the plurality of employers, and the plurality of health plans provided by the plurality of payers for each employer of the plurality of employers. The machine learning model can be utilized to verify the scan data is mapped in accordance with the mapping.

Embodiments of the present invention ensure medical claim reimbursements are timely and enable health care providers to predict cash flow. Embodiments of the present invention provide validated insurance plans by utilizing machine learning techniques which may increase our confidence of health care providers when submitting medical claims for reimbursement. Embodiments of the present invention may provide health care providers additional benefits, such as: a) reduce the need for an extensive local reference build in the electronic health record system; b) reduce the time to complete a local payer and health plan build; c) reduce errors associated with picking the wrong payer or health plan; d) reduce errors associated with routing the correct payer and plan details to the wrong payer; e) provide faster, more accurate, and efficient patient registration with less manual data entry; f) provide a list of valid payer/health plans by employer location; g) enable payer and health plan specific rules to be documented once and leveraged across client domains (e.g., a plurality of health care providers) and platforms without additional build or translation; and h) submit the electronic plan to the correct health plan, as indicated in the electronic eligibility response increases the likelihood the claim will adjudicate without error, potentially resulting in faster payment.

Accordingly, in one aspect, an embodiment is directed to one or more computer storage media having computer-executable instructions embodied thereon that, when executed by a computer, causes the computer to perform operations. The operations include receiving scan data corresponding to an insurance card. The scan data comprises an identification of a payer and an identification of a health plan of the payer. The operations also include receiving transaction data from electronic data interchange (EDI) insurance transactions. The transaction data comprises data corresponding to a plurality of employers, a plurality of payers, and a plurality of health plans provided by the plurality of payers. The operations further include training a machine learning model with the transaction data to build a mapping of the plurality of employers, the plurality of payers contracted with each employer of the plurality of employers, and the plurality of health plans provided by the plurality of payers for each employer of the plurality of employers. The operations also include, utilizing the machine learning model, verifying the scan data is mapped in accordance with the mapping.

In another aspect of the invention, an embodiment of the present invention is directed to a computerized method. The method includes receiving transaction data from electronic data interchange (EDI) insurance transactions. The transaction data comprises data corresponding to a plurality of employers, a plurality of payers, and a plurality of health plans provided by the plurality of payers. The method also includes training a machine learning model with the transaction data to build a mapping of the plurality of employers, the plurality of payers contracted with each employer of the plurality of employers, and the plurality of health plans provided by the plurality of payers for each employer of the plurality of employers.

In a further aspect, an embodiment is directed to a computerized system that includes one or more processors and a non-transitory computer storage medium storing computer-useable instructions that, when used by the one or more processors, cause the one or more processors to: receive scan data corresponding to an insurance card, the scan data comprising an identification of a payer and an identification of a health plan of the payer; and utilize a machine learning model trained to build a mapping of the plurality of employers, the plurality of payers contracted with each employer of the plurality of employers, and the plurality of health plans provided by the plurality of payers for each employer of the plurality of employers to verify the scan data is mapped in accordance with the mapping.

Figure 1:
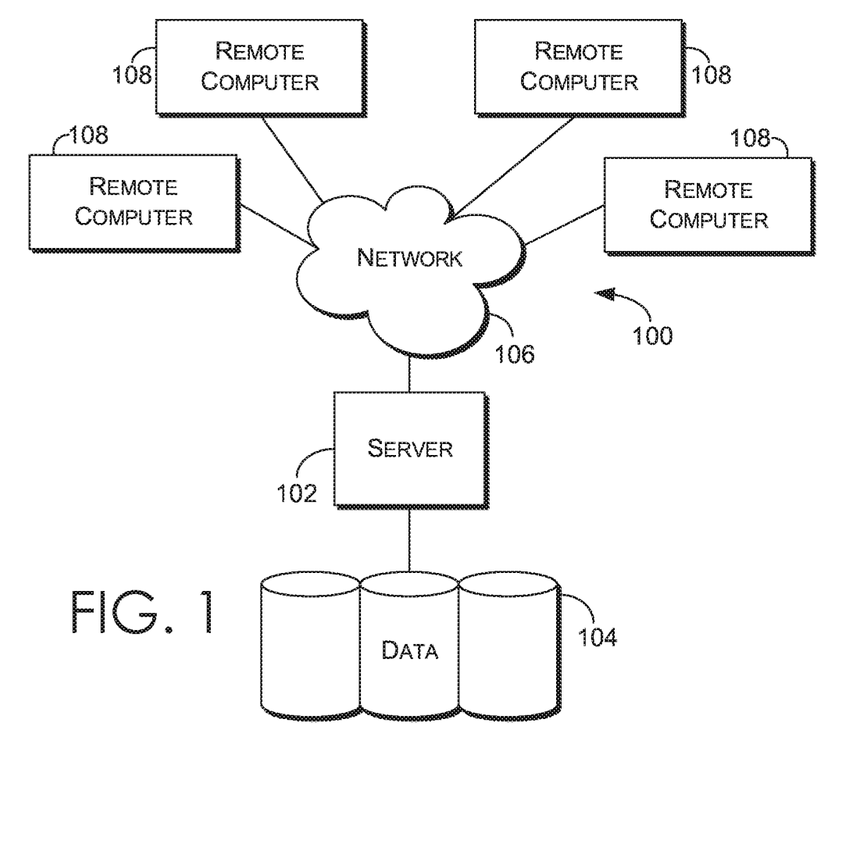
FIG. 1 is a block diagram of an exemplary computing environment suitable for use in implementing the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multi-processor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, ambulatory settings, medical billing and financial offices, hospital administration settings, home healthcare environments, clinicians' offices, Center for Disease Control, Centers for Medicare & Medicaid Services, World Health Organization, any governing body either foreign or domestic, Health Information Exchange, and any healthcare/government regulatory bodies not otherwise mentioned. Clinicians may comprise a treating physician or physicians; specialists such as intensivists, surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
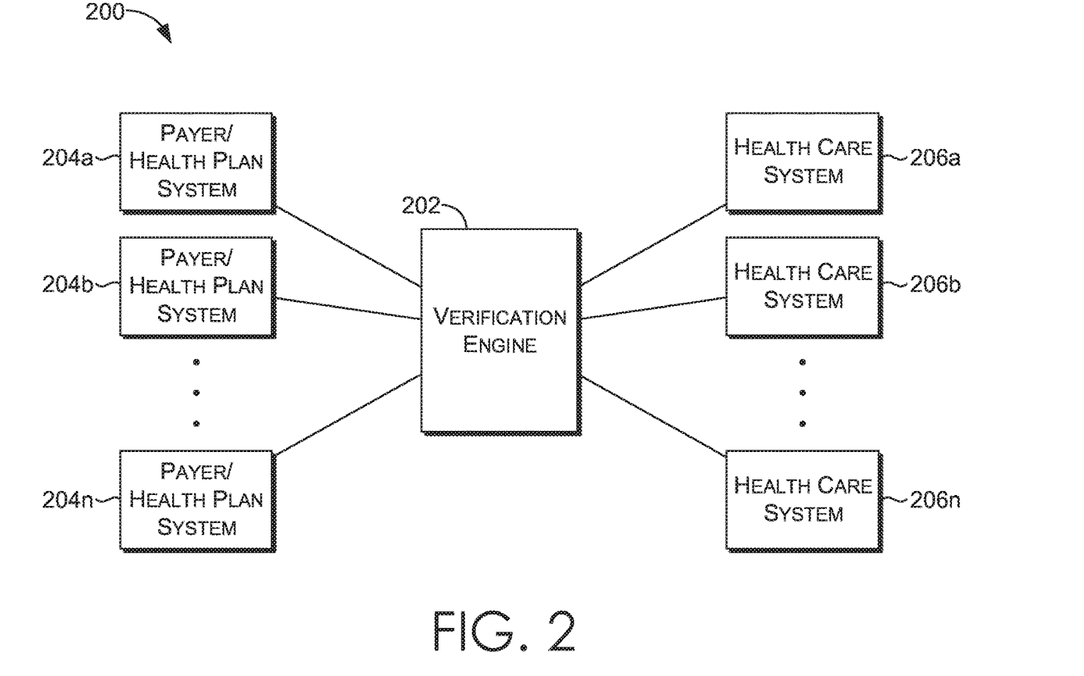
FIG. 2 is a block diagram of an exemplary system for intelligently linking payer/health plan combinations to specific employers, in accordance with an embodiment of the present invention.

Turning now to FIG. 2, an exemplary linking and verification system 200 is depicted suitable for use in implementing embodiments of the present invention. The linking and verification system 200 is merely an example of one suitable computing system environment and is not intended to suggest any limitation as to the scope of use or functionality of embodiments of the present invention. Neither should the linking and verification system 200 be interpreted as having any dependency or requirement related to any single module/component or combination of modules/components illustrated therein.

The linking and verification system 200 includes verification engine 202, payer/health plan system(s) 204a-204n, and health care system(s) 206a-206n all in communication with one another via a network. The network may include, without limitation, one or more secure local area networks (LANs) or wide area networks (WANs). The network may be a secure network associated with a facility such as a healthcare facility. The secure network may require that a user log in and be authenticated in order to send and/or receive information over the network.

The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, verification engine 202, payer/health plan system(s) 204a-204n, and health care system(s) 206a-206n might reside on a server, cluster of servers, or a computing device remote from one or more of the remaining components. Although illustrated as separate systems, verification engine 202, payer/health plan system(s) 204a-204n, and health care system(s) 206a-206n, the functionality provided by each of these components might be provided as a single component/module. For example, components of the verification engine 202 might reside on a payer/health plan system or a health care system. The single unit depictions are meant for clarity, not to limit the scope of embodiments in any form.

Components of the linking and verification system 200 may include a processing unit, internal system memory, and a suitable system bus for coupling various system components, including one or more data stores for storing information (e.g., files and metadata associated therewith). Components of the linking and verification system 200 typically includes, or has access to, a variety of computer-readable media.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

Verification engine 202 generally receives transaction data (e.g., EDI insurance transactions) from payer/health plan system(s) 204a-204n and health care system(s) 206a-206n and trains a machine learning model to build a mapping of a plurality of employers, a plurality of payers contracted with each employer of the plurality of employers, and a plurality of health plans provided by the plurality of payers for each employer of the plurality of employers. For clarity, EDI insurance transactions may include eligibility, claim, claim status, and remittance transactions. The machine learning model can be utilized to verify insurance (e.g., payer/health plan combination) for a patient that presents an insurance card or predict insurance for a patient that does not present an insurance card.

Each of payer/health plan system(s) 204a-204n generally facilitates the exchange of EDI insurance transactions between health care system(s) 206a-206n and a payer. For example, the payer/health plan system(s) 204a-204n may receive transactions corresponding to claims and encounter information, payment and remittance advice, claims status, eligibility, enrollment and disenrollment, referrals and authorizations, coordination of benefits, and premium payments. Each of these transactions may be utilized to facilitate medical claim reimbursements. Moreover, each of these transactions may be utilized by verification engine 202 verify and/or predict payer/health plan combinations.

Each of health care system(s) 206a-206n includes or has access to infrastructure that is capable of storing electronic health records (EHRs) of patients associated with health care system(s) 206a-206n. EHRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, insurance (e.g., payer/health plan) information, employer information, work location, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information. In some embodiments, health care system(s) 206a-206n may receive data from health information exchanges ("HIEs"), personal health records ("PHRs"), patient claims, and other health records associated with a patient.

User device (not shown in FIG. 2) may be any type of computing device used within a healthcare facility or as part of the claims processing process to receive, display, and send information to another user or system. User device may be capable of communicating via the network with verification engine 202, payer/health plan system(s) 204a-204n, or health care system(s) 206a-206n. Such devices may include any type of mobile and portable devices including cellular telephones, personal digital assistants, tablet PCs, smart phones, and the like.

User device is configured to display information to a user via a series of user interfaces. For example, the user interface may include information corresponding to scan data of an insurance card such as an identity of a payer and a health plan of the payer. Additionally, or alternatively, in some embodiments, the scan data comprises an identification of an employer. The user interface may enable a user to review or revise scan data that has been automatically extracted by a card scanning service into appropriate fields of the user interface prior to saving the scan data in an electronic health record of a patient. Additionally, the user interface may provide a display of a front image capture and a back image capture of the insurance card. The user interface may provide employer and work location address information imported from a registration system or an EHR. A filtered list of valid payer/hearth plan combinations for specific employers may also be provided by the user interface. Embodiments are not intended to be limited to visual display but rather may also include audio presentation, visual presentation, combined audio/visual presentation, and the like.

In practice, a patient may present an insurance card to a facility associated with a health care system 206a-206n. The insurance card is scanned and scan data is communicated to verification engine 202. The scan data may include an identification of a payer and an identification of a health plan of the payer. Additionally, or alternatively, in some embodiments, the scan data comprises an identification of an employer. At the same time, the verification engine 202 has been receiving transaction data from EDI insurance transactions. The transaction data comprises data corresponding to a plurality of employers, a plurality of payers, and a plurality of health plans provided by the plurality of payers. The verification engine 202 trains a machine learning model with the transaction data and builds a mapping of the plurality of employers, the plurality of payers contracted with each employer of the plurality of employers, and the plurality of health plans provided by the plurality of payers for each employer of the plurality of employers. Utilizing the trained model, the verification engine 202 can verify the scan data is mapped appropriately and the proper payer/health plan combination is saved to the EHR for the patient.

Alternatively, if the patient fails to provide an insurance card, the trained model can be utilized by the verification engine 202 to predict the payer/health plan combination for the patient. Moreover, as the verification engine 202 receives additional data from the payer/health plan system 204a-204n and/or the health care system 206a-206n, the machine learning model is continuously updated to provide accurate and up-to-date verifications and predictions.

Figure 3:
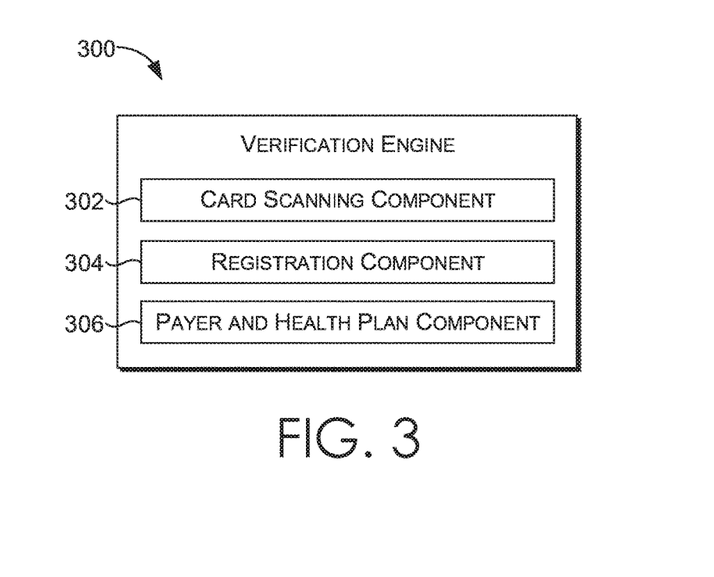
FIG. 3 is a block diagram of an exemplary verification engine, in accordance with an embodiment of the present invention.

In FIG. 3, an exemplary verification engine 300 (such as verification engine 202 of FIG. 2) is depicted suitable for use in implementing embodiments of the present invention. As described above, the verification engine 300 generally receives transaction data (e.g., EDI insurance transactions)

from a payer/health plan system (such as payer/health plan system(s) 204a-204n of FIG. 2) and health care system (such as health care system(s) 206a-206n of FIG. 2) and trains a machine learning model to build a mapping of a plurality of employers, a plurality of payers contracted with each employer of the plurality of employers, and a plurality of health plans provided by the plurality of payers for each employer of the plurality of employers. The machine learning model can be utilized to verify insurance (e.g., payer/health plan combination) for a patient that presents an insurance card or predict insurance for a patient that does not present an insurance card.

As illustrated in FIG. 3, the verification engine 300 includes card scanning component 302, registration component 304, and payer and health plan component 306.

The card scanning component 302 generally receives scan data corresponding to an insurance card. The scan data comprises an identification of a payer and an identification of a health plan of the payer. Additionally, or alternatively, in some embodiments, the scan data comprises an identification of an employer. Optical character recognition (OCR) may be utilized by the card scanning component to automatically extract data from the insurance card into appropriate text fields.

The registration component 304 generally provides a user interface that enables a user to view the front and back of the card image capture, review OCR field capture, and manually correct any information prior to saving the scan data to the EHR. Additionally, the registration component 304 may provide a user interface that enables a user to view employer and work location address information important from a registration system of a health care system or manually enter the employer name and work location address information. In some embodiments, the registration component 304 provides a user interface that enables a user to view a filtered list of valid payer/health plan combinations for a specific employer, such as when a patient does not present an insurance card, and select the appropriate plan.

The payer and health plan component 306 generally receives verifies or predicts insurance information. To do so, the payer and health plan component 306 initially utilizes the payer name from the insurance card to capture a payer display name. The health plan name from the insurance card is also utilized to capture a health plan display name. Using X12N 271 eligibility responses, the payer and health plan component 306 records payer's name and payer's identification from transactions (e.g., NM1*PR*2*ABC COMPANY*****PI*842610001~, where ABC COMPANY is the payer's name and 842610001 is the payer's identification). The X12N 271 eligibility responses can also be utilized to capture plan begin and plan end dates (e.g., DTP*346*D8*20060101~). The payer and health plan component 306 verifies payers that have name and identification and valid begin plan dates. Verified payers are provided with a system generated unique payer identification.

The payer and health plan component 306 utilizes X12N 271 eligibility responses to record insurance type codes and the plan coverage description (e.g., EB*B**1^33^35^47^86^88^98AALAMHAUC*HM*GOLD 123 PLAN*27*10*****Y_, where HM is the insurance type code and GOLD 123 is the plan coverage description). Receipt of paid X12N 835 remittances are utilized to confirm valid payer name and plan coverage name (description) combinations. Health plans with insurance type codes and plan coverage descriptions with valid being plan dates are verified and have a system generated unique health plan identification.

Figure 4:
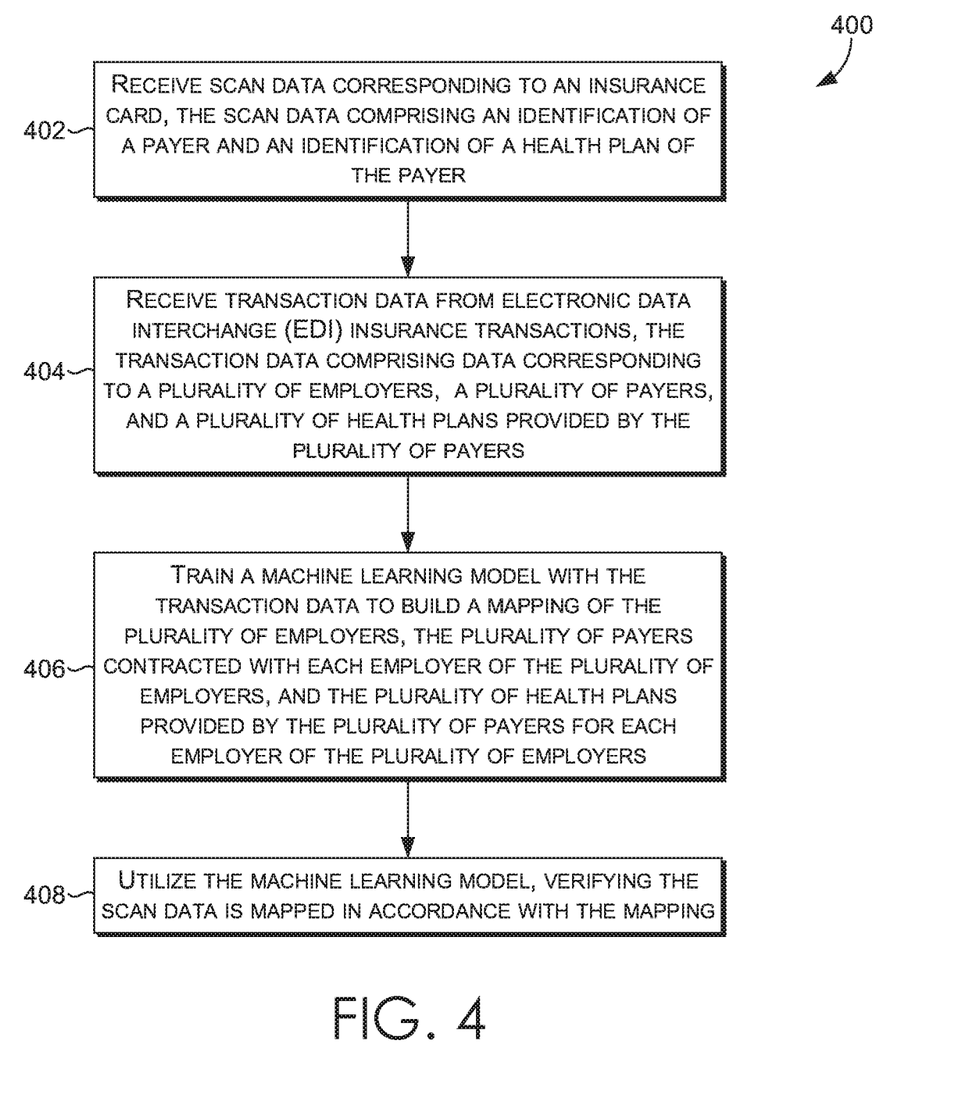
FIG. 4 is a flow diagram showing an exemplary method utilizing a machine learning model to verify payers and health plans, in accordance with various embodiments of the present invention.

Turning now to FIG. 4, a flow diagram is provided illustrating a method 400 for training and utilizing a machine learning model to verify payers and health plans, in accordance with an embodiment of the present invention. Method 400 may be performed by any computing device (such as computing device described with respect to FIG. 1) with access to a linking and verification system (such as the one described with respect to FIG. 2) or by one or more components of the linking and verification system (such as components of the verification engine described with respect to FIG. 3).

Initially, as shown at step 402, scan data corresponding to an insurance card is received. The scan data comprises an identification of a payer and an identification of a health plan of the payer. Additionally, or alternatively, in some embodiments, the scan data comprises an identification of an employer.

At step 404, transaction data is received from EDI insurance transactions. The transaction data comprises data corresponding to a plurality of employers, a plurality of payers, and a plurality of health plans provided by the plurality of payers.

At step 406, a machine learning model is trained with the transaction data to build a mapping of the plurality of employers, the plurality of payers contracted with each employer of the plurality of employers, and the plurality of health plans provided by the plurality of payers for each employer of the plurality of employers.

At step 408, the machine learning model is utilized to verify the scan data is mapped in accordance with the mapping.

In some embodiments, a user interface is provided that displays fields for the identification of the payer, the identification of the health plan of the payer, and the identification of the employer. A card scanning service may automatically extract the scan data into appropriate fields of the user interface. The extracted scan data may comprise the identification of the payer, the identification of the health plan of the payer, and the identification of the employer. The user interface enables a user to review or revise the extracted scan data prior to saving the scan data in an electronic health record of a patient.

The user interface may also provide a view of a front image capture and a view of a back image capture of the insurance card. Additionally, the user interface may provide a view of employer and work location address information that has been imported from a registration system or an EHR. In some embodiments, the user interface displays a filtered list of valid payer/health plan combinations for specific employers. The user is enabled to select, via the user interface, a payer/health plan combination for a patient from the filtered list of valid payer/health plan combinations. For example, if the patient does not present an insurance card but provides employer and work location information, the system may be able to predict payer/health plan combinations that are likely to have the patient enrolled.

Figure 5:
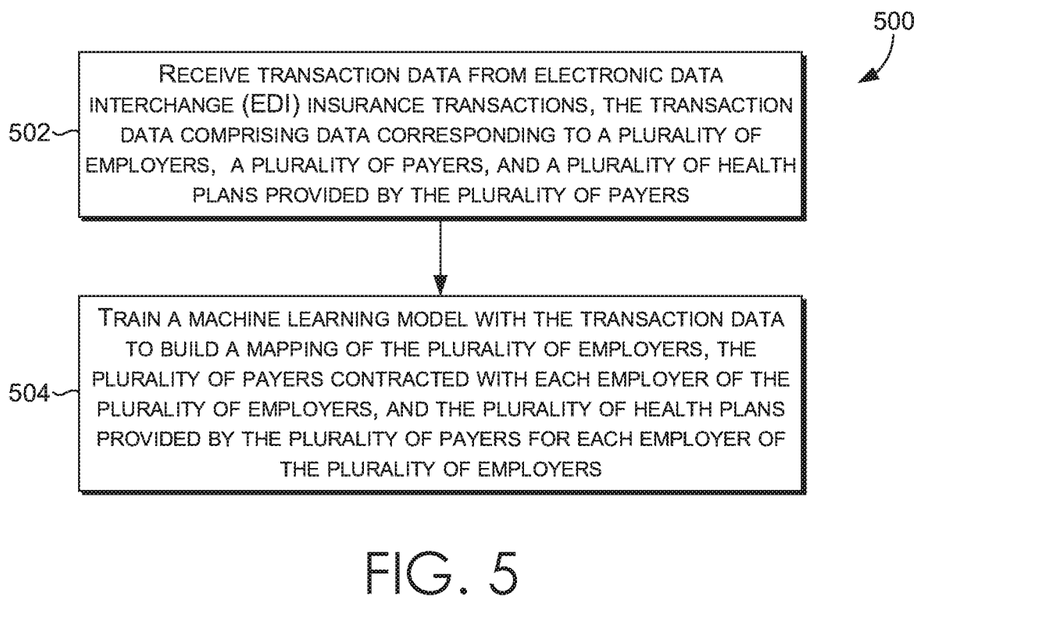
FIG. 5 is a flow diagram showing an exemplary method for training a machine learning model to verify payers and health plans, in accordance with various embodiments of the present invention.

Referring now to FIG. 5 a flow diagram is provided illustrating a method 500 for training a machine learning model to verify payers and health plans, in accordance with an embodiment of the present invention. Method 500 may be performed by any computing device (such as computing device described with respect to FIG. 1) with access to a linking and verification system (such as the one described with respect to FIG. 2) or by one or more components of the linking and verification system (such as components of the verification engine described with respect to FIG. 3).

Initially, as shown at step 502, transaction data is received from EDI insurance transactions. The transaction data comprises data corresponding to a plurality of employers, a plurality of payers, and a plurality of health plans provided by the plurality of payers.

At step 504 a machine learning model is trained with the transaction data to build a mapping of the plurality of employers, the plurality of payers contracted with each employer of the plurality of employers, and the plurality of health plans provided by the plurality of payers for each employer of the plurality of employers.

In some embodiments, scan data corresponding to an insurance card is received. The scan data comprises an identification of a payer, an identification of a health plan of the payer. Additionally, or alternatively, in some embodiments, the scan data comprises an identification of an employer. The machine learning model may be utilized to verify the scan data is mapped in accordance with the mapping.

In some embodiments, a patient may not have an insurance card but is able to provide an identification of an employer and a work location. The machine learning model may be utilized to predict one or more payer/health plan combinations based on the received identification of the employer and the work location.

In some embodiments, a user is enabled via a user interface to select a payer/health plan combination of the one or more payer/health plan combinations. The selected payer/health plan combination may be saved in an electronic health record of a patient.

Figure 6:
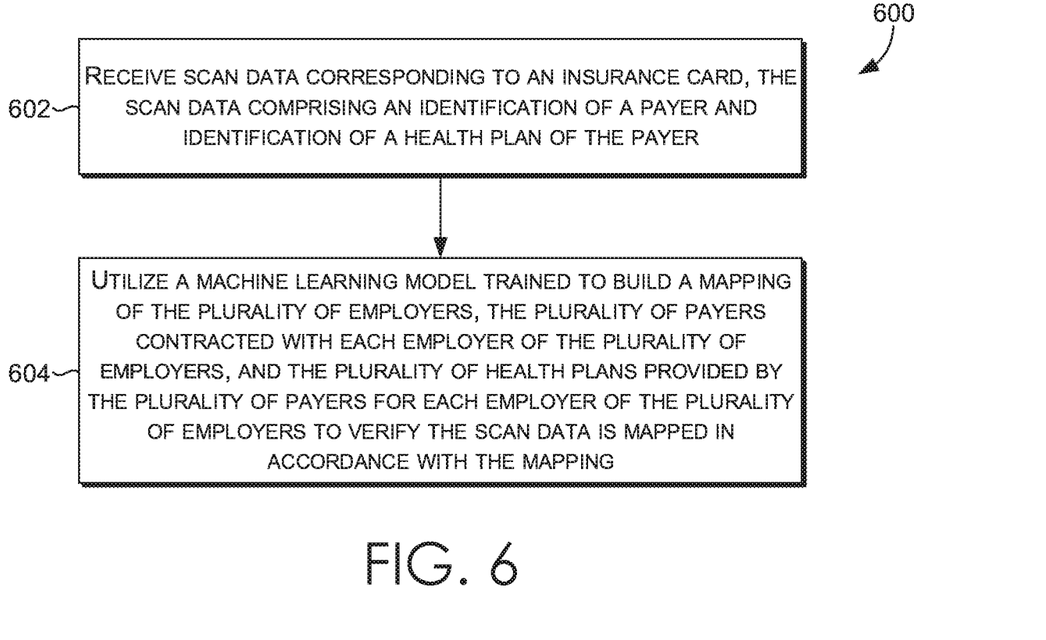
FIG. 6 is a flow diagram showing an exemplary method for utilizing a machine learning model to verify payers and health plans, in accordance with various embodiments of the present invention.

In FIG. 6, a flow diagram illustrates a method 600 for utilizing a machine learning model to verify payers and health plans, in accordance with an embodiment of the present invention. Method 600 may be performed by any computing device (such as computing device described with respect to FIG. 1) with access to a linking and verification system (such as the one described with respect to FIG. 2) or by one or more components of the linking and verification system (such as components of the verification engine described with respect to FIG. 3).

Initially, as shown at step 602, scan data corresponding to an insurance card is received. The scan data comprises an identification of a payer and an identification of a health plan of the payer. Additionally, or alternatively, in some embodiments, the scan data comprises an identification of an employer.

At step 604, a machine learning model that has been trained to build a mapping of a plurality of employers, a plurality of payers contracted with each employer of the plurality of employers, and a plurality of health plans provided by the plurality of payers for each employer of the plurality of employers is utilized to verify the scan data is mapped in accordance with the mapping. Additionally, or alternatively, the machine learning model may be trained to build the mapping based on home addresses and/or physical location of employment of the patients.

The machine learning model may be trained with transaction data received from EDI insurance transactions. The transaction data comprises data corresponding to a plurality of employers, a plurality of payers, and a plurality of health plans provided by the plurality of payers. During training, the machine learning model builds the mapping of the plurality of employers, the plurality of payers contracted with each employer of the plurality of employers, and the plurality of health plans provided by the plurality of payers for each employer of the plurality of employers. As additional information is received, such as reimbursements or denials, the machine learning model continues to update the mapping of the plurality of employers, the plurality of payers contracted with each employer of the plurality of employers, and the plurality of health plans provided by the plurality of payers for each employer of the plurality of employers to reflect billing successes and failures.

In some embodiments, a user interface is provided that displays fields for the identification of the payer, the identification of the health plan of the payer, and the identification of the employer. The scan data may automatically be extracted by a card scanning service into appropriate fields of the user interface. The user interface enables a user to review or revise the extracted scan data prior to saving the scan data in an electronic health record.

As can be understood, the present invention provides systems, methods, and user interfaces for training and utilizing a machine learning model to verify payers and health plans. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. A non-transitory computer-readable medium storing computer-executable instructions that, when executed by a computer including a processor, cause the computer to perform functions comprising:
   training a machine learning model to predict a payer/health plan combination for a patient by:
      receiving transaction data from electronic data interchange (EDI) insurance transactions, the transaction data comprising data corresponding to a plurality of employers, a plurality of payers contracted with each employer of the plurality of employers, and a plurality of health plans provided by the plurality of payers for each employer of the plurality of employers;
      extracting a first dataset of features from the received transaction data: and
      training the machine learning model to predict a payer/health plan combination for a patient by inputting the first dataset into the machine learning model to build a mapping of the plurality of employers, the plurality of payers contracted with each employer of the plurality of employers, and the plurality of health plans provided by the plurality of payers for each employer of the plurality of employers;
      receiving additional transaction data from the EDI insurance transactions, the additional transaction data comprising reimbursements or denials;
      extracting a second dataset of features from the additional transaction data; and
      inputting the second dataset into the machine learning model to update the mapping;
   obtaining employer and work location data associated with a patient who does not present an insurance card;
   creating a patient dataset from the obtained employer and work location data: and inputting the patient dataset into the machine learning model to predict, for the patient who does not present an insurance card, one or more payer/health plan combinations based on the employer and work location information.

2. The non-transitory computer-readable medium of claim 1, further comprising instructions that, when executed by at least the processor, cause the processor to:
provide a user interface that displays fields for the identification of the payer, the identification of the health plan of the payer, and the identification of the employer.

3. The non-transitory computer-readable medium of claim 2, further comprising instructions that, when executed by at least the processor, cause the processor to:
automatically extract, at a card scanning service, scan data into appropriate fields of the user interface, the scan data corresponding to an insurance card and comprising the identification of the payer and the identification of the health plan of the payer.

4. The non-transitory computer-readable medium of claim 3, further comprising instructions that, when executed by at least the processor, cause the processor to:
enable a user, via the user interface, to review or revise the extracted scan data prior to saving the extracted scan data in an electronic health record of a patient.

5. The non-transitory computer-readable medium of claim 3, wherein the extracted scan data comprises the identification of the payer, the identification of the health plan of the payer, and the identification of the employer.

6. The non-transitory computer-readable medium of claim 3, further comprising instructions that, when executed by at least the processor, cause the processor to:
display, at the user interface, a view of a front image capture and a view of a back image capture of the insurance card.

7. The one non-transitory computer-readable medium of claim 3, further comprising instructions that, when executed by at least the processor, cause the processor to:
display, at the user interface, employer and work location address information imported from a registration system.

8. The non-transitory computer-readable medium of claim 3, further comprising instructions that, when executed by at least the processor, cause the processor to:
display, at the user interface, a filtered list of valid payer/health plan combinations for specific employers.

9. The non-transitory computer-readable medium of claim 8, further comprising instructions that, when executed by at least the processor, cause the processor to:
enable, via the user interface, a user to select a payer/health plan combination for a patient.

10. A method for predicting a payer/health plan combination for a patient comprising:
training a machine learning model to predict a payer/health plan combination for a patient by:
receiving transaction data from electronic data interchange (EDI) insurance transactions, the transaction data comprising data corresponding to a plurality of employers, a plurality of payers contracted with each employer of the plurality of employers, and a plurality of health plans provided by the plurality of payers for each employer of the plurality of employers;
extracting a first dataset of features from the received transaction data: and
training a machine learning model to predict a payer/health plan combination for a patient by inputting the first dataset into the machine learning model to build a mapping of the plurality of employers, the plurality of payers contracted with each employer of the plurality of employers, and the plurality of health plans provided by the plurality of payers for each employer of the plurality of employers;
receiving additional transaction data from the EDI insurance transactions, the additional transaction data comprising reimbursements or denials;
extracting a second dataset of features from the additional transaction data; and
inputting the second dataset into the machine learning model to update the mapping;
obtaining employer and work location data associated with a patient who does not present an insurance card;
creating a patient dataset from the obtained employer and work location data: and
inputting the patient dataset into the machine learning model to predict, for the patient who does not present an insurance card, one or more payer/health plan combinations based on the employer and work location information.

11. The method of claim 10, further comprising receiving scan data corresponding to an insurance card, the scan data comprising an identification of a payer and an identification of a health plan of the payer.

12. The method of claim 10, wherein the method further comprises:
utilizing the machine learning model to verify that the scan data is mapped in accordance with the mapping.

13. The method of claim 10, wherein the method further comprises:
receiving an identification of an employer and a work location.

14. The method of claim 13, wherein the method further comprises:
utilizing the machine learning model, to predict one or more payer/health plan combinations based on the identification of the employer and the work location.

15. The method of claim 14, wherein the method further comprises:
enabling a user, via a user interface, to select a payer/health plan combination of the one or more payer/health plan combinations.

16. The method of claim 15, wherein the method further comprises:
saving the selected payer/health plan combination in an electronic health record of a patient.

17. A computerized system comprising:
one or more processors; and
a non-transitory computer storage media storing computer-useable instructions that, when used by the one or more processors, cause the one or more processors to:
train a machine learning model to predict a payer/health plan combination for a patient by:
receiving transaction data from electronic data interchange (EDI) insurance transactions, the transaction data comprising data corresponding to a plurality of employers, a plurality of payers contracted with each employer of the plurality of employers, and a plurality of health plans provided by the plurality of payers for each employer of the plurality of employers;
extracting a first dataset of features from the received transaction data: and
training a machine learning model to predict a payer/health plan combination for a patient by inputting the first dataset into the machine learning model to build a mapping of the plurality of employers, the plurality of payers contracted with each employer of the plurality of employers, and the plurality of health plans provided by the plurality of payers for each employer of the plurality of employers;

receive additional transaction data from the EDI insurance transactions, the additional transaction data comprising reimbursements or denials:

extract a second dataset of features from the additional transaction data;

input the second dataset into the machine learning model to update the mapping;

obtain employer and work location data associated with a patient who does not present an insurance card;

create a patient dataset from the obtained employer and work location data; and input the patient dataset into the machine learning model, predict to predict, for the patient who does patients that do not present an insurance card, one or more payer/health plan combinations based on the employer and work location information.

18. The system of claim 17, wherein the computer-executable instructions are further configured to cause the at least one or more processors to:

provide a user interface that displays fields for the identification of the payer, the identification of the health plan of the payer, and the identification of the employer;

automatically extract, at a card scanning service, scan data into appropriate fields of the user interface, the scan data corresponding to an insurance card and comprising the identification of the payer and the identification of the health plan of the payer; and enable, via the user interface, a review or a revision of the extracted scan data prior to saving the extracted scan data in an electronic health record.

* * * * *